(12) United States Patent
Haziza et al.

(10) Patent No.: US 11,076,891 B2
(45) Date of Patent: Aug. 3, 2021

(54) BI-DIRECTIONAL MOTION SPINAL IMPLANT

(71) Applicant: Premia Spine Ltd., Ramat Poleg (IL)

(72) Inventors: Rafi Haziza, Kiryat Bialik (IL); Uri Arnin, Kiryat Tivon (IL)

(73) Assignee: Premia Spine Ltd., Ramat Poleg (IL)

( * ) Notice: Subject to any disclaimer, the term of this patent is extended or adjusted under 35 U.S.C. 154(b) by 102 days.

(21) Appl. No.: 16/449,403

(22) Filed: Jun. 23, 2019

(65) Prior Publication Data

US 2020/0397483 A1 Dec. 24, 2020

(51) Int. Cl.
*A61B 17/70* (2006.01)
*A61B 17/86* (2006.01)

(52) U.S. Cl.
CPC ...... *A61B 17/7049* (2013.01); *A61B 17/8625* (2013.01); *A61B 17/8605* (2013.01)

(58) Field of Classification Search
CPC ........... A61B 17/7049; A61B 17/8625; A61B 17/8605; A61B 17/705; A61B 17/7052; A61B 17/7061; A61B 17/864; A61B 17/866; A61B 17/861; A61B 17/8615; A61B 17/7071; A61B 17/7014; A61B 17/8009; A61B 17/802; A61B 17/8023; A61B 17/645; A61B 17/62; A61B 17/64; A61B 17/704; A61B 17/7037; A61B 17/7032; A61B 17/7002
USPC ................................................ 606/246–279
See application file for complete search history.

(56) References Cited

U.S. PATENT DOCUMENTS

| | | | | |
|---|---|---|---|---|
| 7,837,714 | B2* | 11/2010 | Drewry | A61B 17/7052 606/250 |
| 10,413,330 | B2* | 9/2019 | Cowan | A61B 17/7052 |
| 2004/0181223 | A1* | 9/2004 | Ritland | A61B 17/7014 606/258 |
| 2005/0131406 | A1 | 6/2005 | Reiley | |
| 2006/0095132 | A1 | 5/2006 | Kirschman | |
| 2008/0172090 | A1* | 7/2008 | Molz | A61F 2/4425 606/246 |
| 2011/0040331 | A1* | 2/2011 | Fernandez | A61B 17/701 606/264 |
| 2012/0083845 | A1 | 4/2012 | Winslow | |
| 2014/0088649 | A1 | 3/2014 | Refai | |
| 2017/0311986 | A1* | 11/2017 | McNab | A61B 17/708 |

FOREIGN PATENT DOCUMENTS

| | | |
|---|---|---|
| EP | 3391859 | 10/2018 |
| WO | 2006/020530 | 2/2006 |
| WO | 2006/102443 | 9/2006 |
| WO | 2007/043044 | 4/2007 |
| WO | 2008/134703 | 11/2008 |

OTHER PUBLICATIONS

PCT Search Report and Written Opinion PCT/IB2020/055657, dated Oct. 30, 2020.

* cited by examiner

*Primary Examiner* — Pedro Philogene
(74) *Attorney, Agent, or Firm* — Dekel Patent Ltd.; David Klein

(57) ABSTRACT

A spinal implant includes first and second pedicle screws, each of which comprises a threaded shank coupled to a head. First and second cantilevered arms are coupled to the first and second pedicle screws, respectively. The first cantilevered arm includes a contact member arranged to contact and move over a contact portion of the second cantilevered arm.

13 Claims, 6 Drawing Sheets ically to a spinal implant that permits bi-directional motion for dynamic stabilization of adjacent vertebrae.

BI-DIRECTIONAL MOTION SPINAL IMPLANT

FIELD OF THE INVENTION

The present invention relates generally to methods and apparatus for minimally invasive surgery on spinal structures, and particularly to a spinal implant that permits bi-directional motion for dynamic stabilization of adjacent vertebrae.

BACKGROUND OF THE INVENTION

Posterior lumbar or transforaminal lumbar surgical procedures involve placement of a spinal implant secured by pedicle screws and neural decompression, all of which are done through posterior incisions, which are kept to a minimum in minimally invasive surgery.

For example, dynamic stabilization techniques have been developed for the posterior spine. These posterior techniques utilize pedicle screws and a dynamic rod. Typically the dynamic rod has a mechanism to bend under certain loads or forces, thereby absorbing some stress and strain that is applied to the spine.

SUMMARY OF THE INVENTION

The present invention seeks to provide a spinal implant that permits bi-directional motion for dynamic stabilization of adjacent vertebrae, as described in more detail further below.

There is thus provided in accordance with a non-limiting embodiment of the present invention a spinal implant including first and second pedicle screws, each of which includes a threaded shank coupled to a head, and first and second cantilevered arms coupled to the first and second pedicle screws, respectively, wherein the first cantilevered arm includes a contact member arranged to contact and move over a contact portion of the second cantilevered arm.

In one embodiment, an outer contour of the head is convex, and each of the first and second cantilevered arms includes a concave inner portion, and the first and second cantilevered arms are secured to the first and second pedicle screws, respectively, with a fastener that presses the concave inner portion against the outer contour of the head.

In one embodiment, a fastener-interface portion of each of the first and second cantilevered arms is convex, and the fastener includes a concave inner portion configured to press against the fastener-interface portion.

In one embodiment, the first and second cantilevered arms are parallel to each other.

In one embodiment, the contact member is convex and the contact portion is concave.

In one embodiment, the contact member includes a round roller element.

In one embodiment, the second cantilevered arm includes at least one side wall that straddles the contact member.

In one embodiment, the contact member is pivotally coupled to the first cantilevered arm.

In one embodiment, the contact member is fixedly coupled to the first cantilevered arm.

In one embodiment, the contact member is movable independently of both the first and second cantilevered arms.

In one embodiment, the contact member has a different hardness than the contact portion.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
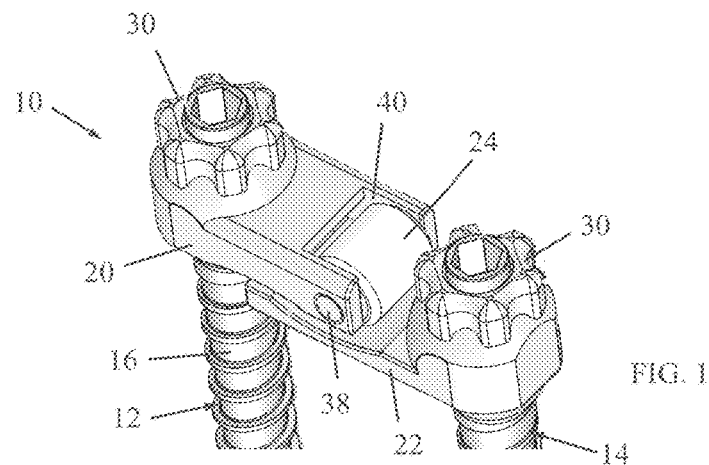
FIGS. 1, 1A and 1B are simplified perspective, front-view and sectional illustrations of a spinal implant, constructed and operative in accordance with a non-limiting embodiment of the present invention.
Figure 1A:
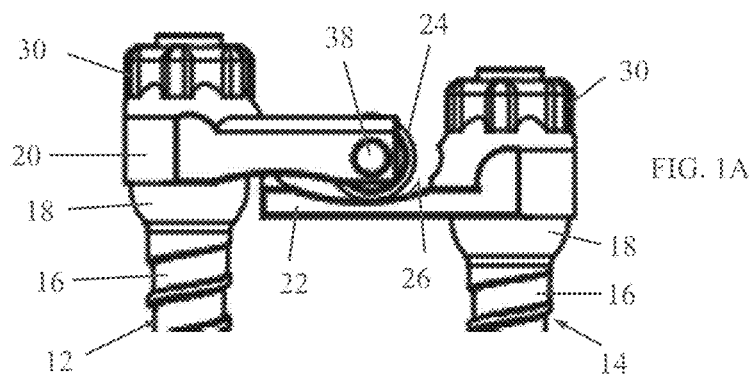
Figure 1B:
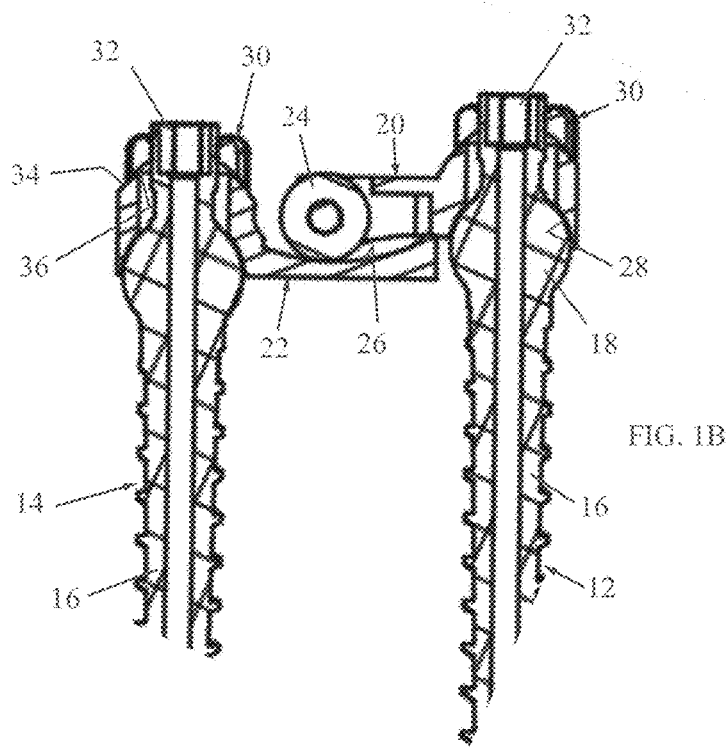

Reference is now made to FIGS. 1-1B, which illustrate a spinal implant 10, constructed and operative in accordance with a non-limiting embodiment of the present invention.

The spinal implant 10 includes first and second pedicle screws 12 and 14. Each screw includes a threaded shank 16 coupled to a head 18, which may be a polyaxial head. First and second cantilevered arms 20 and 22 are coupled to the first and second pedicle screws 12 and 14, respectively. The first cantilevered arm 20 includes a contact member 24 arranged to contact and move over a contact portion 26 of the second cantilevered arm 22.

The outer contour of head 18 may be convex. Each of the first and second cantilevered arms 20 and 22 includes a concave inner portion 28 (FIG. 1B) complementarily shaped to match the curvature of the head 18. The first and second cantilevered arms 20 and 22 may be secured to the first and second pedicle screws 12 and 14, respectively, with a fastener 30 that presses the concave inner portion 28 against the outer contour of the head 18. For example, in the illustrated embodiment, fastener 30 includes a male-threaded portion 32 (FIG. 1B) that engages female thread formed in an upper portion of head 18.

In one embodiment, a fastener-interface portion 34 (FIG. 1B) of each of the first and second cantilevered arms 20 and 22 is convex. The fastener 30 includes a concave inner portion 36 configured to press against the fastener-interface portion 34, as seen in FIG. 1B.

Due to the convex-concave interface between the fastener and the cantilevered arms and between the cantilevered arms and the pedicle screw head, the first and second cantilevered arms 20 and 22 may be secured to the first and second pedicle screws 12 and 14, respectively, at any angular orientation along the contour of the pedicle screw head 18. This provides the surgeon with limitless possibilities of mounting the spinal implant 10 in the patient first and second cantilevered arms 20 and 22 directed at any desired direction. For example, in the illustrations, the first and second cantilevered arms 20 and 22 are parallel to each other; however, they can be non-parallel, such as by tilting one or both of the arms over the outer contour of the head 18.

In the illustrated embodiment, the contact member 24 is convex and the contact portion 26 is concave. The contact member 24 may be a round roller element, such as a cylindrical roller bearing element which rolls about pivots 38 and which fits in a recess 40 formed in first cantilevered arm 20. Thus, in this embodiment, the contact member 24 is pivotally coupled to the first cantilevered arm 20.

Figure 2:
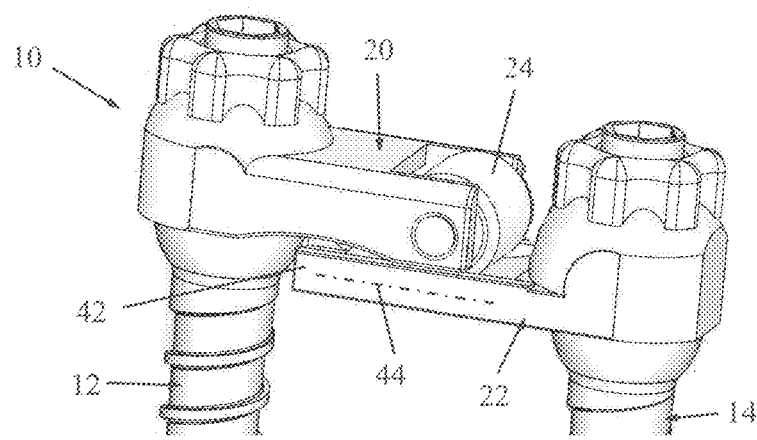
FIGS. 2, 2A and 2B are simplified perspective, front-view and sectional illustrations of a spinal implant, in accordance with another non-limiting embodiment of the present invention.
Figure 2A:
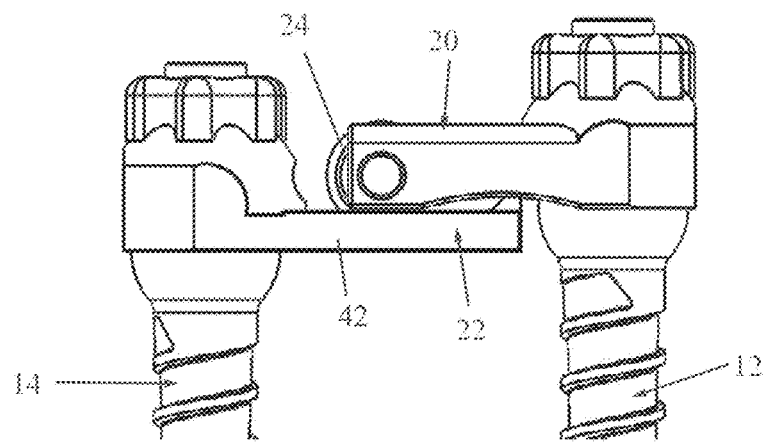
Figure 2B:
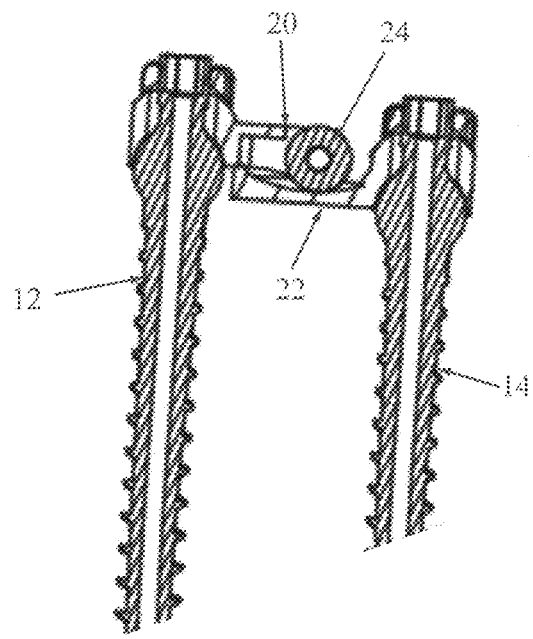

Reference is now made to FIGS. 2-2B, which illustrate a modified version of the spinal implant 10, with like elements designated by like numerals. In this version, second cantilevered arm 22 includes at least one side wall 42 that straddles contact member 24. The first cantilevered arm 20 is arranged to move over second cantilevered arm 22 in two linear directions (back and forth) along a longitudinal axis 44 of the arms 20 and 22. In reality, other motion may also occur (e.g., perpendicular or otherwise tilted with respect to longitudinal axis 44), due to imperfections or manufacturing tolerances, or due to the chosen rotational orientation of the arms with respect to the round outer contours of heads 18. The side wall 42 may be useful to limit the non-longitudinal movement and ensure that contact member 24 of first cantilevered arm 20 does not slip off second cantilevered arm 22.

Figure 3:
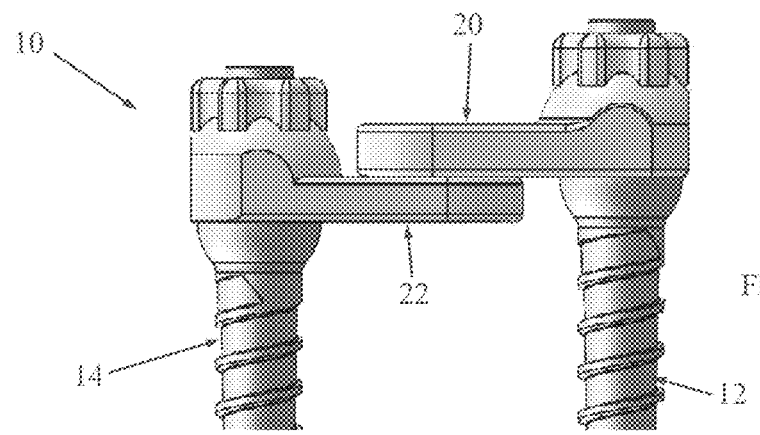
FIGS. 3, 3A and 3B are simplified perspective, front-view and sectional illustrations of a spinal implant, in accordance with another non-limiting embodiment of the present invention.
Figure 3A:
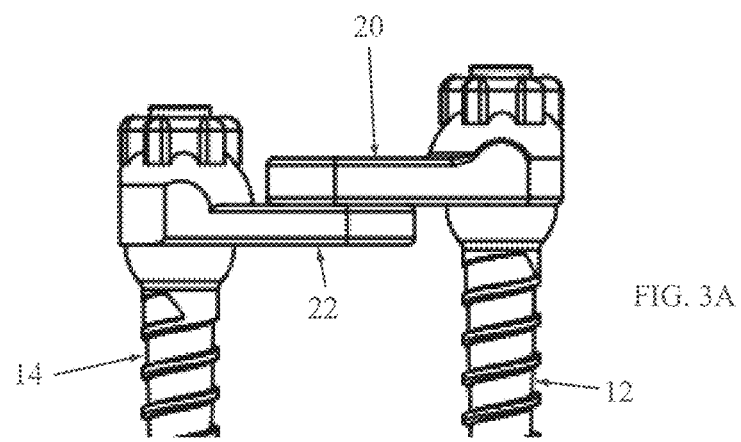
Figure 3B:
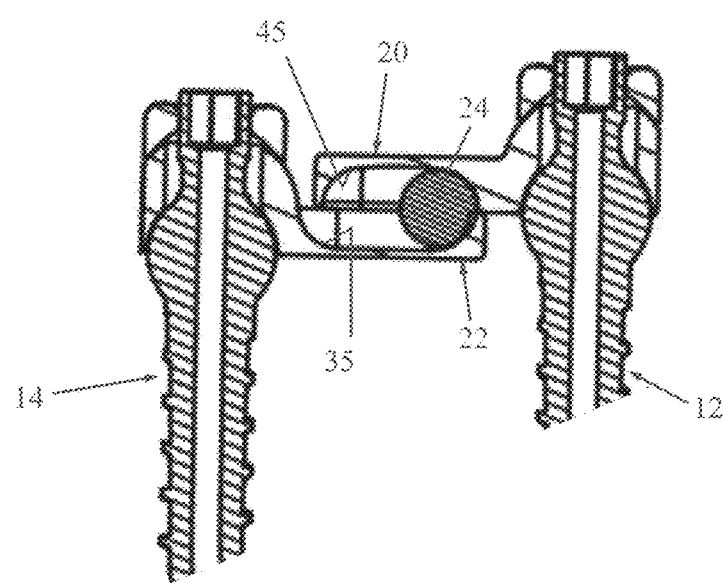

Reference is now made to FIGS. 3-3B, which illustrate a modified version of the spinal implant 10, with like elements designated by like numerals. In this version, the contact member 24 (FIG. 3B), e.g., a sphere, is movable independently of both the first and second cantilevered arms 20 and 22. This is in contrast with the other embodiments, in which the contact member is fixedly coupled to the first cantilevered arm 20. In this embodiment, both the first and second cantilevered arms 20 and 22 may be formed with a concave inner portion 35 (FIG. 3B) to accommodate the shape of contact member 24.

Figure 4:
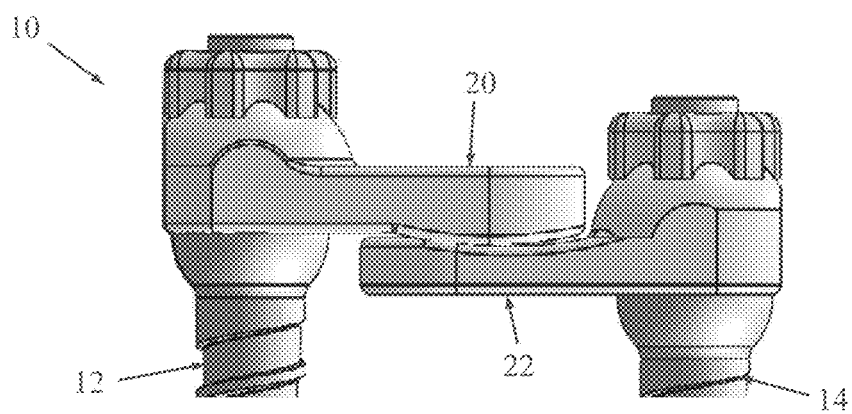
FIGS. 4, 4A and 4B are simplified perspective, front-view and sectional illustrations of a spinal implant, in accordance with another non-limiting embodiment of the present invention.
Figure 4A:
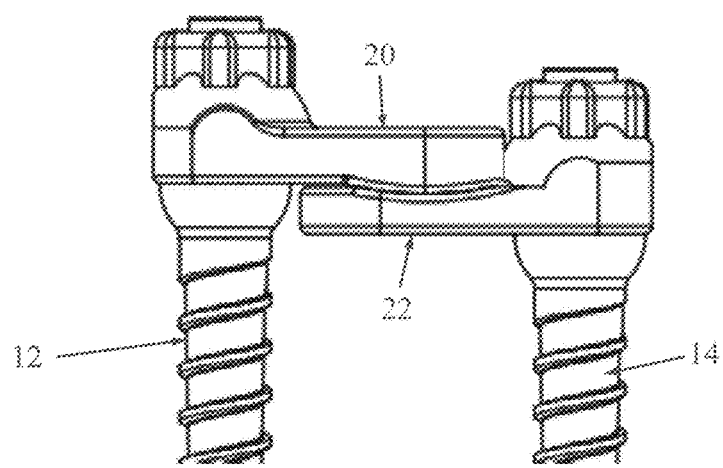
Figure 4B:
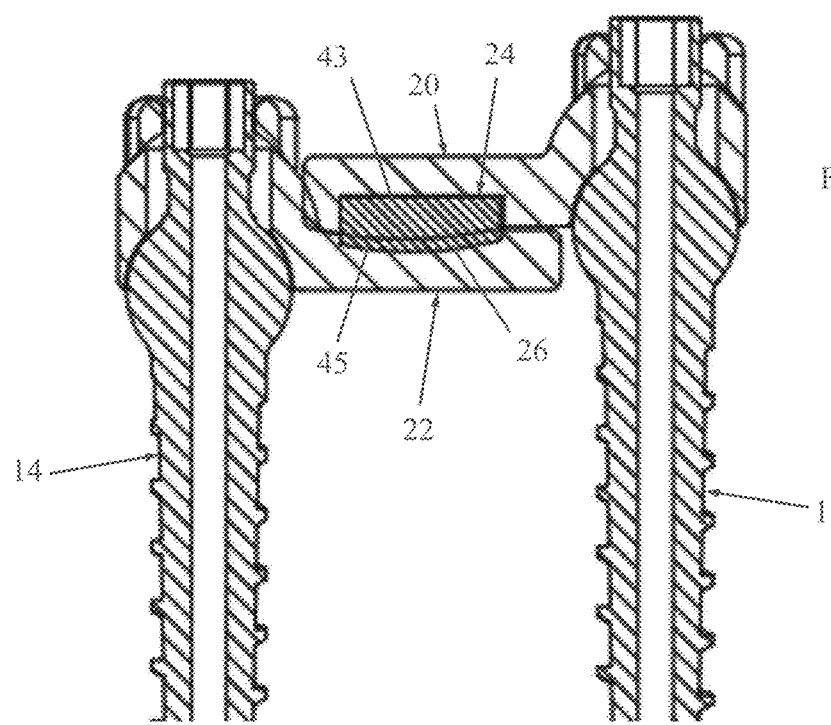

Reference is now made to FIGS. 4-4B, which illustrate a modified version of the spinal implant 10, with like elements designated by like numerals. In this version, the contact member 24 (FIG. 4B) has an upper flat face 43 and a lower convex contact face 45 for contacting the concave contact portion 26 of the second cantilevered arm 22.

Figure 5:
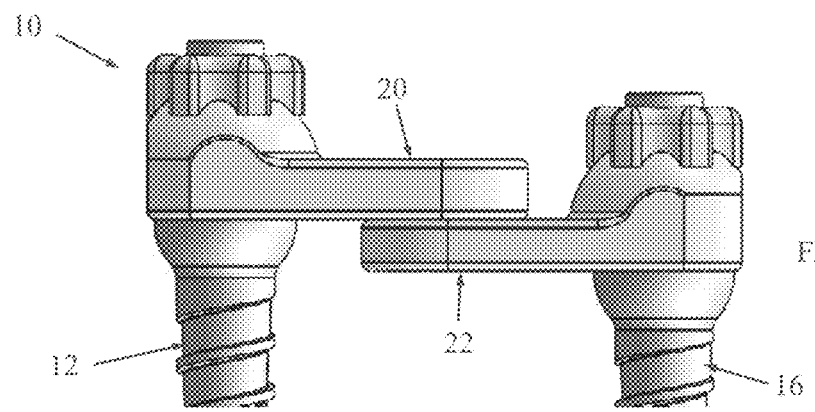
FIGS. 5, 5A and 5B are simplified perspective, front-view and sectional illustrations of a spinal implant, in accordance with another non-limiting embodiment of the present invention.
Figure 5A:
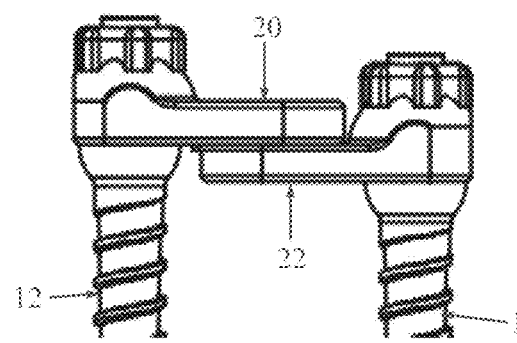
Figure 5B:
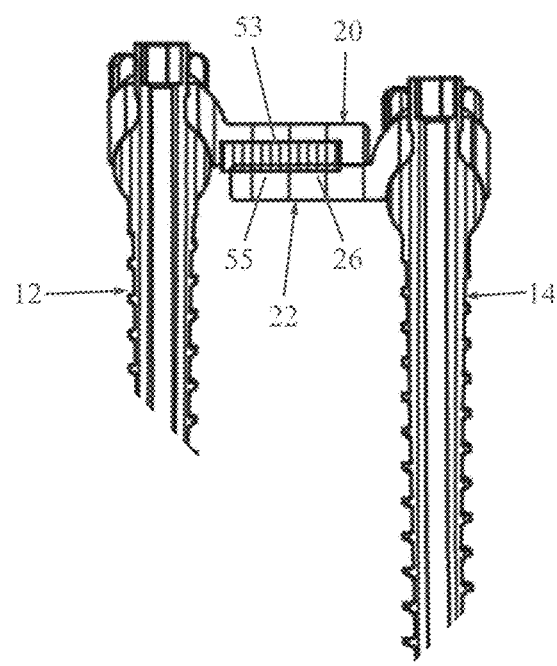

Reference is now made to FIGS. 5-5B, which illustrate a modified version of the spinal implant 10, with like elements designated by like numerals. In this version, the contact member 24 (FIG. 5B) has an upper flat face 53 and a lower flat contact face 55 for contacting the flat contact portion 26 of the second cantilevered arm 22.

Figure 6:
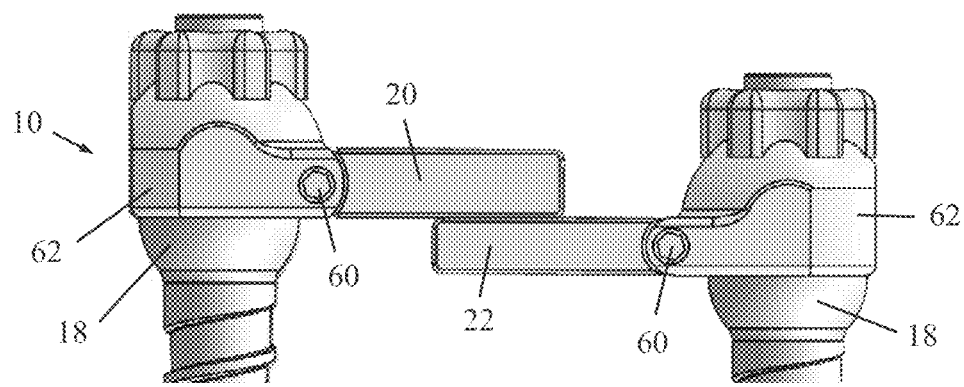
FIGS. 6, 6A and 6B are simplified perspective, front-view and sectional illustrations of a spinal implant, in accordance with another non-limiting embodiment of the present invention.
Figure 6A:
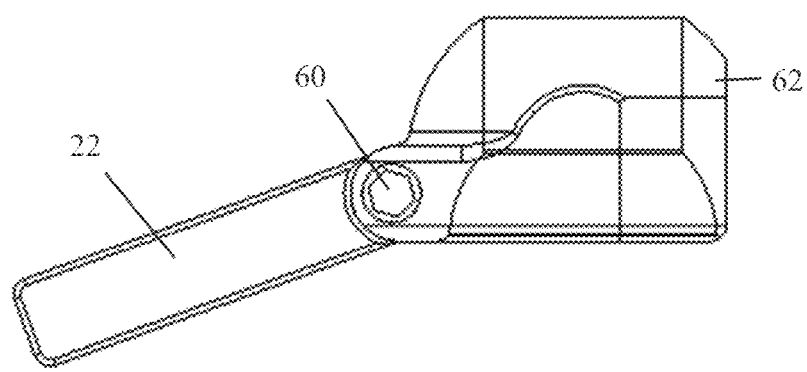
Figure 6B:
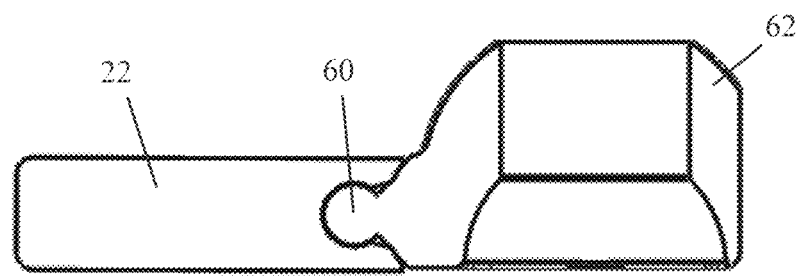

Reference is now made to FIGS. 6-6B, which illustrate a modified version of the spinal implant 10, with like elements designated by like numerals. In this version, the first and second cantilevered arms 20 and 22 are each pivoted about a pivot 60 with respect to a base member 62 that fits over the head 18. The pivot 60 may be a ball-and-socket joint (as in FIG. 6B); additionally or alternatively it may be a locking screw (as in FIG. 6A) or a ratchet which can lock the first and second cantilevered arms 20 and 22 at any desired angle. The contact member 24 and the contact portion 26 are shown as flat but may be any of the other configurations of the other embodiments.

In all embodiments, the contact member 24 may have the same or a different hardness (softer or harder) than the contact portion 26.

What is claimed is:

1. A spinal implant comprising:
   first and second pedicle screws, each of which comprises a threaded shank coupled to a head; and
   first and second cantilevered arms coupled to said first and second pedicle screws, respectively, wherein said first cantilevered arm comprises a rollable contact member arranged to contact and move over a contact portion of said second cantilevered arm, said rollable contact member being movable in rotation and translation.

2. The spinal implant according to claim 1, wherein an outer contour of said head is convex, and each of said first and second cantilevered arms comprises a concave inner portion, and said first and second cantilevered arms are secured to said first and second pedicle screws, respectively, with a fastener that presses said concave inner portion against said outer contour of said head.

3. The spinal implant according to claim 2, wherein a fastener-interface portion of each of said first and second cantilevered arms is convex, and said fastener comprises a concave inner portion configured to press against said fastener-interface portion.

4. The spinal implant according to claim 1, wherein said first and second cantilevered arms are parallel to each other.

5. The spinal implant according to claim 1, wherein said contact member is convex and said contact portion is concave.

6. The spinal implant according to claim 1, wherein said contact member comprises a round roller element, which is cylindrical or spherical.

7. The spinal implant according to claim 1, wherein said second cantilevered arm comprises at least one side wall that straddles said contact member.

8. The spinal implant according to claim 1, wherein said contact member is pivotally coupled to said first cantilevered arm.

9. The spinal implant according to claim 1, wherein said contact member is fixedly coupled to said first cantilevered arm.

10. The spinal implant according to claim 1, wherein said contact member is movable independently of both said first and second cantilevered arms.

11. The spinal implant according to claim 1, wherein said first and second cantilevered arms are each pivoted about a pivot with respect to a base member that fits over said head.

12. The spinal implant according to claim 1, wherein said contact member has a different hardness than said contact portion.

13. The spinal implant according to claim 1, wherein said contact member is movable 360° in rotation without hindrance.

* * * * *